US00PP34805P3

(12) United States Plant Patent
Blom

(10) Patent No.: US PP34,805 P3
(45) Date of Patent: Dec. 6, 2022

(54) ***HEMEROCALLIS* PLANT NAMED 'VER00329'**

(50) Latin Name: ***Hemerocallis* hybrid**
Varietal Denomination: 'VER00329'

(71) Applicant: Heemskerk Vasteplanten BV, Noordwijk (NL)

(72) Inventor: Arie Blom, Vleuten (NL)

(73) Assignee: HEEMSKERK VASTEPLANTEN B V, Noordwijk (NL)

( * ) Notice: Subject to any disclaimer, the term of this patent is extended or adjusted under 35 U.S.C. 154(b) by 0 days.

(21) Appl. No.: 17/670,958

(22) Filed: Feb. 14, 2022

(65) Prior Publication Data

US 2022/0264780 P1 Aug. 18, 2022

(30) Foreign Application Priority Data

Feb. 15, 2021 (QZ) ..... 20210215

(51) Int. Cl.
*A01H 5/02* (2018.01)
*A01H 6/56* (2018.01)

(52) U.S. Cl.
USPC ..... Plt./312
CPC ..... *A01H 6/56* (2018.05)

(58) Field of Classification Search
USPC ..... Plt./312, 263.1
CPC ... A01H 5/02; A01H 5/00; A01H 5/12; A01H 6/00; A01H 6/56
See application file for complete search history.

(56) References Cited

PUBLICATIONS

CPVO Register 4.1.47, retrieved on Mar. 29, 2022 at https://online.plantvarieties.eu/publicConsultationDetails?registerId=20210215&denomination=ver00329, 2 pp. (Year: 2022).*

* cited by examiner

*Primary Examiner* — June Hwu
(74) *Attorney, Agent, or Firm* — Penny J. Aguirre

(57) ABSTRACT

A new cultivar of *Hemerocallis* plant named 'VER00329' that is characterized by its flowers that are dark yellow in color, its long and continuous blooming habit; blooming from mid-June to mid-September in the Netherlands, its compact plant habit, and its deciduous growth habit (dormant in winter).

3 Drawing Sheets

Botanical classification: *Hemerocallis* hybrid.
Cultivar designation: 'VER00329'.

CROSS-REFERENCE TO A RELATED APPLICATION

This application claims priority to European Community Plant Variety Office (CPVO) Plant Breeder's Rights Application No. 2021/0215 filed on Feb. 15, 2021, under 35 U.S.C. 119(f), the entire contents of which is incorporated by reference herein.

BACKGROUND OF THE INVENTION

The present invention relates to a new and distinct cultivar of *Hemerocallis* plant of hybrid origin, botanically known as *Hemerocallis* 'VER00329' and will be referred to hereafter by its cultivar name, 'VER00329'. 'VER00329' is a new cultivar of herbaceous daylily grown for use in the landscape and as a container plant.

The new cultivar was developed through an on-going breeding program conducted by the Inventor in Noordwijk, The Netherlands. The objectives of the breeding program are to develop new cultivars of *Hemerocallis* with long and continuous blooming habits combined with compact and clump forming plant habits.

The new cultivar arose from crosses made in summer of 2005. Unnamed and unpatented proprietary female parents were pollinated with a mixture of pollen collected from unnamed and unpatented proprietary male parents and the resulting seeds from the crosses were pooled and sown for evaluation. 'VER00329' was selected as a single unique plant from the resulting seedlings in summer of 2007. The specific parents are therefore unknown.

Asexual propagation of the new cultivar was first accomplished by division in Noordwijk, The Netherlands in 2008 by the Inventor. Asexual propagation by division has determined that the characteristics of this cultivar are stable and are reproduced true to type in successive generations.

SUMMARY OF THE INVENTION

The following traits have been repeatedly observed and represent the characteristics of 'VER00329'. These attributes in combination distinguish 'VER00329' as a new and distinct cultivar of *Hemerocallis*.

1. 'VER00329' exhibits flowers that are dark yellow in color.
2. 'VER00329' exhibits a long and continuous blooming habit; blooming from mid-June to mid-September in the Netherlands.
3. 'VER00329' exhibits a compact plant habit.
4. 'VER00329' exhibits a deciduous growth habit (dormant in winter).

The new cultivar can be most closely compared to *Hemerocallis* cultivars 'Stella d'Oro' (not patented) and 'Happy Returns' (not patented). 'Stella d'Oro' and 'Happy Returns' are both similar to 'VER00329' in having a dormant growth habit in winter, an extended flowering period, and flowers that are yellow in color. 'Stella d'Oro' differs from 'VER00329' in having flowers that are lighter yellow in color, a taller plant height, flowers are held closer to the foliage, and a less floriferous blooming habit (fewer flowering stems). 'Happy Returns' differs from 'VER00329' in having flowers that are lighter yellow in color, a taller plant height, a less floriferous blooming habit, and flowers that are larger in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to publications from European plant trials.

BRIEF DESCRIPTION OF THE DRAWINGS

The accompanying color photographs illustrate the overall appearance and distinct characteristics of the new *Hemerocallis*. The photographs were taken of a 12-month-old plant as grown in a conventional greenhouse with lightly chalked glass in a 17-cm container in Noordwijk, The Netherlands.

The photograph in FIG. 1 provides a side view of 'VER00329' in bloom.

Figure 1:
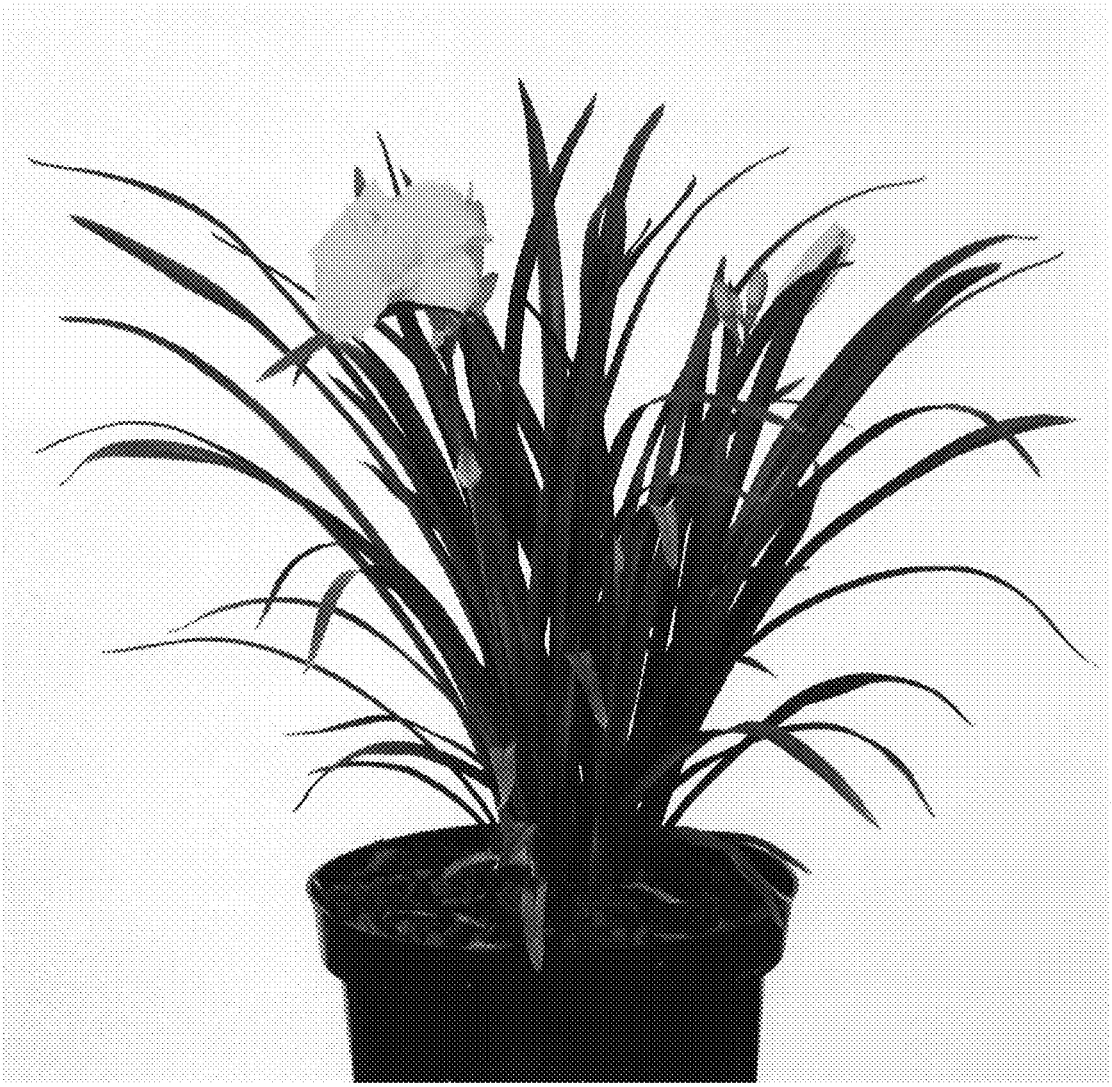
Figure 2:
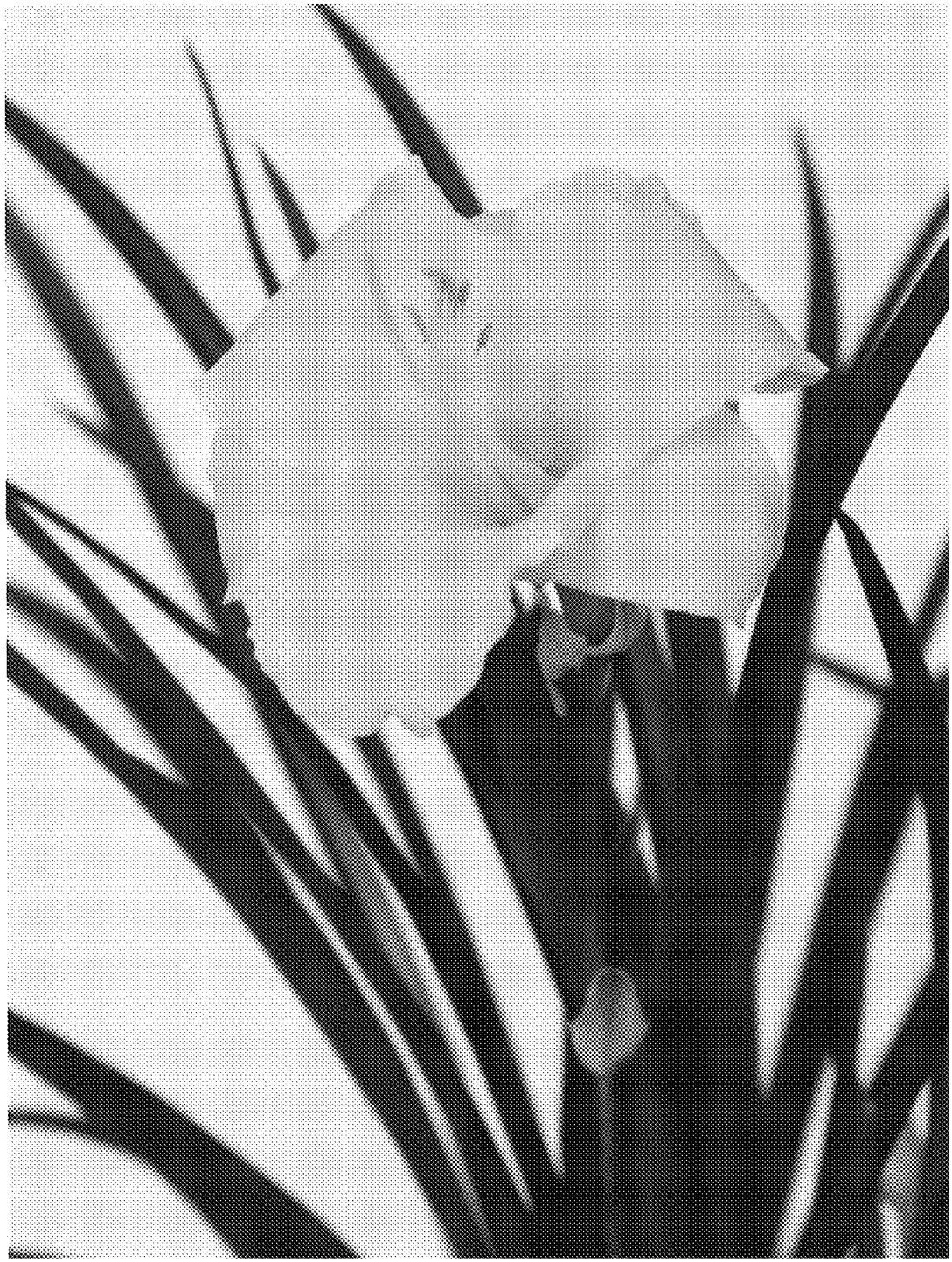

The photograph in FIG. 2 provides a close-up view of a flower of 'VER00329'.

Figure 3:
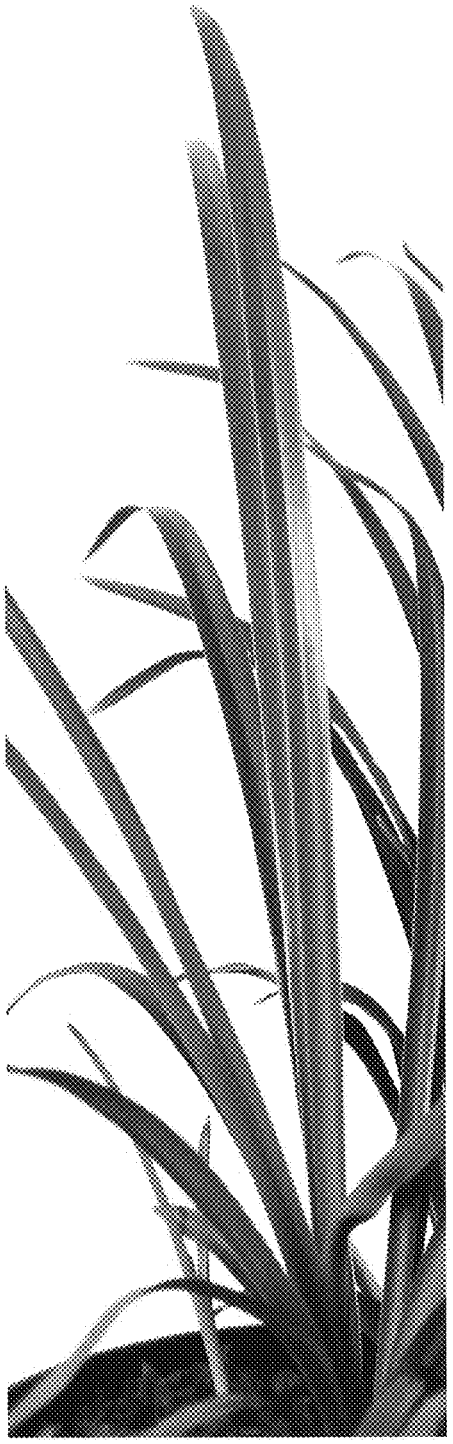

The photograph in FIG. 3 provides a close-up view of the foliage of 'VER00329'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 12-month-old plants of the new cultivar as grown in a conventional greenhouse with lightly chalked glass in 17-cm containers in Noordwijk, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

- *Blooming period.*—3 months, mid-June to mid-September in The Netherlands.
- *Plant type*.—Herbaceous perennial.
- *Plant habit*.—Compact, upright with arching leaves, dormant type, broadly spreading.
- *Height and spread*.—Reaches an average of 31.7 cm in height from soil level to top of foliar plane, 29.2 cm in height from soil level to top of floral plane, and 45.3 cm in spread.
- *Cold hardiness*.—At least in U.S.D.A. Zone 4.
- *Diseases and pests*.—No susceptibility or resistance to diseases or pests has been observed.
- *Root description*.—Fleshy with fibrous secondary roots.
- *Propagation type*.—Division.
- *Root development*.—About 16 weeks to produce a salable young plant from a single fan division.
- *Growth rate*.—Moderately vigorous.

Foliage description:

- *Leaf shape*.—Linear.
- *Leaf division*.—Simple.
- *Leaf base*.—Decurrent.
- *Leaf apex*.—Long acute with a mucronate outer tip.
- *Leaf venation*.—Parallel, color upper surface; 143A, color lower surface; NN137B.
- *Leaf margins*.—Entire.
- *Leaf attachment*.—Decurrent, no petioles.
- *Leaf arrangement*.—Basal rosette.
- *Leaf orientation*.—Held upright to pendulant.
- *Leaf surface*.—Both surfaces glabrous, upper surface moderately glossy, lower surface matte.
- *Leaf color*.—Young leaves upper surface; a blend of 144A and 144B, young leaves lower surface; 144A, mature leaves upper surface; a blend of NN137A and 147A, covered with a thin waxy layer of 189A, mature lower surface; 137A.
- *Leaf size*.—Up to 35.5 cm in length, an average of 1 cm in width.
- *Leaf quantity*.—Average of 7 per rosette, 11 leaves per shoot.

Flower description:

- *Inflorescence type*.—Scape bearing a panicle of single flowers.
- *Inflorescence size*.—8.6 cm (excluding peduncle), 9.9 cm in diameter.
- *Lastingness of flowers*.—Average of 1 day, self-cleaning.
- *Flower size*.—An average of 7.5 cm in height, 7.1 cm in diameter, 7.3 cm in depth, throat; 6 mm in diameter, tube; 1.9 cm in length, 6.5 mm in diameter.
- *Flower fragrance*.—None.
- *Flower number*.—Average of 7 per inflorescence, 24 flower buds per plant.
- *Flower aspect*.—Upright to outward.
- *Flower type*.—Campanulate, freely flowering.
- *Flower bud*.—Narrow oblong in shape, average of 4.6 cm in length and 1.1 cm in width, color 154B, base 144B to 144C, tip 143A.
- *Petals* (*inner tepals*).—3, obovate in shape, strongly reflexed, average of 7.4 cm in length and 4 cm in width, margins entire, moderately undulate and finely ruffled, apex broadly retuse, base fused (lower 25.5%), color: upper surface when opening and fully open; 13A, margins 13C, lower surface when opening and fully open; 14C, margins 14D, throat; 13A, flushed with 153D, veins 13B, tube; N144A.
- *Sepals* (*outer tepals*).—3, rotate in arrangement, average of 7.2 cm in length, 2.6 cm in width, shape is obovate and strongly reflexed, margins are entire, slightly to finely undulate, base 26% fused, acute apex, upper surface texture is smooth, glabrous, and matte, velvety in appearance, lower surface texture is smooth, glabrous and very slightly glossy, color: when opening and fully open upper surface; 13A, margins 13B, veins at base 144B, when opening and fully open lower surface; 15A, margins 13B, veins at base 144B.

*Peduncles*.—Smooth and glabrous surface, round in shape, average of 22 cm in length, 3 mm, diameter, held in an average angle of 10°, strong in strength, color 137B, covered with a thin waxy layer N138D, bracts; average of 1 per peduncle, broadly lanceolate in shape, cuneate base, apex acute with cuspidate tip, margins entire with notch on each side, an average of 2.5 cm in length and 1.5 cm in width, color a blend of 155D and 144A.

*Pedicels*.—Smooth and glabrous surface, round in shape, average of 3 mm in length, 2 mm in diameter, held in an average angle of 35°, strong in strength, color 143A.

Reproductive organs:

*Gynoecium*.—Pistil; 1, average of 6.9 cm in length, style; 6.85 cm in length, 13B in color, stigma; crested, 10D in color, 0.05 mm in length and diameter, ovary; oblong in shape, 144C in color.

*Androecium*.—Stamens; 6, anthers; dorsifixed and narrow oblong in shape, 4.5 mm in length, 1 mm in width, 197A in color; filament; 4.1 cm in length, 17B in color, pollen; abundant in quantity and 17A in color.

*Fruit/seeds*.—None observed.

It is claimed:

1. A new and distinct cultivar of *Hemerocallis* plant named 'VER00329' as herein illustrated and described.

* * * * *